United States Patent
Nakagawa et al.

(10) Patent No.: US 7,024,922 B1
(45) Date of Patent: Apr. 11, 2006

(54) VISCOELASTIC CHARACTERISTIC VALUE-MEASURING APPARATUS AND METHOD OF MEASURING VISCOELASTIC CHARACTERISTIC VALUE

(75) Inventors: Noritoshi Nakagawa, 360, 2-chome, Kagamiyama, Higashihiroshima-shi, Hiroshima (JP); Yasuhisa Sekiguchi, Hiroshima (JP); Kiyoto Maruoka, Hyogo (JP); Jun Nishibayashi, Hyogo (JP); Seigo Sakagami, Hyogo (JP); Hiroshi Yoshinaga, Hyogo (JP); Kaname Yamada, Hyogo (JP)

(73) Assignees: SRI Sports Limited, Hyogo (JP); Noritoshi Nakagawa, Hiroshima (JP)

( * ) Notice: Subject to any disclaimer, the term of this patent is extended or adjusted under 35 U.S.C. 154(b) by 0 days.

(21) Appl. No.: 09/607,324

(22) Filed: Jun. 30, 2000

(30) Foreign Application Priority Data

| Jul. 2, 1999 | (JP) | ................... 11-188584 |
| Jun. 13, 2000 | (JP) | ................... 2000-176443 |
| Jun. 13, 2000 | (JP) | ................... 2000-176596 |

(51) Int. Cl.
*G01N 11/10* (2006.01)

(52) U.S. Cl. ...................... 73/760; 73/12.01

(58) Field of Classification Search ............. 73/760, 73/763
See application file for complete search history.

(56) References Cited

U.S. PATENT DOCUMENTS

| 6,672,141 B1 * | 1/2004 | Maruoka et al. ........... 73/54.39 |
| 6,695,719 B1 * | 2/2004 | Maruoka .................... 473/378 |

FOREIGN PATENT DOCUMENTS

EP    0 849 583 A1    6/1998

OTHER PUBLICATIONS

Document 1—Impact Engineering, Nikkan Kogyo Newspaper Ltd, Oct. 28, 1988 pp. 173-183.
Document 2—Lecture thesis of 16th Series of Chugoku Branch of Japan Design Engineering Society Association, Jun. 20, 1988, pp. 25-29.
Lindholm, J. Mech. Phys. Solids, vol. 12, pp. 317-335 (1964).
Zhao et al., Int. J. Impact Engng., vol. 19, No. 4, pp. 319-330 (1997).
Xue et al., Measurement Science and Technology, vol. 6, No. 11, pp. 1557-1565 (1995).
Al-Maliky et al., Meas. Sci., Technol., vol. 7, pp. 746-752 (1996).
Albertini et al., Institute of Physics Conference Series No. 21, vol. 21, pp. 22-32 (Apr. 1974).
Staab et al., Experimental Mechanics, Society for Experimental Stress Analysis, vol. 31, No. 3, pp. 232-235 (Sep. 1991).

* cited by examiner

*Primary Examiner*—Max Noori
*Assistant Examiner*—Andre Allen
(74) *Attorney, Agent, or Firm*—Birch, Stewart, Kolasch & Birch, LLP

(57) ABSTRACT

A viscoelastic characteristic value-measuring apparatus, using a split Hopkinson's bar, having an impact bar, input bar, and an output bar. The input bar has a first strain gauge and a second strain gauge. The output bar has a third strain gauge and a fourth strain gauge. The input bar and the output bar are made of a viscoelastic material, and a specimen is in between the input bar and the output bar. The length of said output bar is set to a range from 500 mm to 2500 mm both inclusive. The length of said input bar is set to a range from 1500 mm to 2500 mm both inclusive.

23 Claims, 5 Drawing Sheets

VISCOELASTIC CHARACTERISTIC VALUE-MEASURING APPARATUS AND METHOD OF MEASURING VISCOELASTIC CHARACTERISTIC VALUE

BACKGROUND OF THE INVENTION

1. Field of the Invention

The present invention relates to an apparatus and a method of measuring a viscoelastic characteristic value such as Young's modulus, a loss factor, and the like of a viscoelastic material such as synthetic resin, crosslinked rubber, and the like. More particularly, the present invention is intended to measure the viscoelastic characteristic value of the viscoelastic material accurately by using a so-called split Hopkinson's bar.

2. Description of the Related Art

In recent years, to analyze the deformation and behavior of an object to which an impact is applied, simulation is used rather than measurement. In the simulation, it is necessary to perform substitutions of the viscoelastic characteristic value (parameter) such as the Young's modulus, the loss factor, and the like of the object. The parameter is classified into a static parameter and a dynamic parameter. Because the deformation and behavior of the object is dynamic, the dynamic parameter measured in a state close to the deformation and behavior is effective for the simulation. The measurement of the dynamic parameter is also important for apprehending the characteristic of the object.

As means for measuring the dynamic parameter, an apparatus using the split Hopkinson's bar is known. The split Hopkinson's bar is used in the field of metal material (see page 173–183 of "Impact Engineering" published by Nikkan Kogyo Newspaper Ltd. on Oct. 28, 1989) or the like. In the apparatus using the split Hopkinson's bar, an impact bar, an input bar, and an output bar all made of metal are arranged in a straight line; a specimen is held between the rear end of the input bar and the front end of the output bar; and a strain gauge is installed on each of the input bar and the output bar.

In measuring the viscoelastic characteristic of the specimen, the front end of the input bar is hit by the impact bar. A strain wave generated at the impact time propagates to the specimen and the output bar from the input bar. The following three waves are measured with gauges installed on the input bar and the output bar to compute the viscoelastic characteristic value of the specimen: An incident strain wave progressing in the input bar to its rear end, a reflected strain wave reflected from the rear end of the input bar and progressing to its front end, and a transmitted strain wave transmitted from the rear end of the input bar to the rear end of the output bar through the specimen.

It is to be noted that in the description made below the incident strain wave, the reflected strain wave, and the transmitted strain wave are abbreviated as a "strain wave" as necessary and that the input bar and the output bar are abbreviated as a "stress bar" as necessary.

The measuring apparatus is capable of measuring the characteristic value of a metal material but has difficulty in measuring the viscoelastic characteristic value of a polymer such as synthetic resin, crosslinked rubber, and the like. When the specimen is made of the polymer, there is a large difference between the characteristic impedance of the specimen and that of the stress bar made of metal. This is because it is difficult to pick up the strain wave propagating in the input bar, the specimen, and the output bar correctly. In measuring the viscoelastic characteristic value of the polymer, it is necessary to select the stress bar having a small difference between the characteristic impedance thereof and that of the specimen.

A viscoelastic characteristic value-measuring apparatus using the stress bar made of the polymer instead of the metal bar is disclosed by Nakagawa of Hiroshima University and others on pages 25–29 of lecture thesis of 16th series of Chugoku Branch of Japan Design Engineering Society Association. Unlike the stress bar made of metal, the strain wave is attenuated greatly in the stress bar made of the polymer. For example, the incident strain wave progressing in the input bar to the specimen is attenuated before it reaches the rear end of the input bar after it is measured with a strain gauge installed on the input bar. Thus, it is impossible to correctly assume the incident strain wave at the rear end of the input bar. Similarly, it is impossible to correctly assume the reflected strain wave reflected from the rear end of the input bar and progressing to the front end thereof and the transmitted strain wave transmitted to the output bar from the rear end of the specimen.

In the viscoelastic characteristic value-measuring apparatus disclosed by Nakagawa and others, two strain gauges are installed on each of the input bar and the output bar to solve the problem of the damp of the stress bar made of the polymer. That is, a transmission function is derived from the incident strain wave, the reflected strain wave, and the transmitted strain wave measured with the two strain gauges. From the transmission function, the strain amount of each of the incident strain wave at the rear end of the input bar, the reflected strain wave at the rear end of the input bar, and the transmitted strain wave at the front end of the output bar are estimated. The viscoelastic characteristic value-measuring apparatus is capable of measuring the viscoelastic characteristic value of the specimen when the specimen deforms greatly at high speed (maximum strain speed: 500–8000 per second) and in a large amount (maximum deformation amount is in the range from 1% to 30%).

The viscoelastic characteristic value-measuring apparatus is capable of correctly measuring the viscoelastic characteristic value of a comparatively hard polymer, but has a large error in measuring the viscoelastic characteristic value of a comparatively soft viscoelastic material. The error is attributed to the fact that as the specimen becomes softer, the difference between the progress speed of the strain wave in the specimen and that thereof in the input bar and the output bar disposed forward and rearward from the specimen becomes increasingly large.

That is, in the case of the specimen made of the comparatively soft viscoelastic material, the progress speed of the strain wave is higher in the input bar than in the specimen. The strain wave is reflected by its rear end. When the input bar is short, a first reflected strain wave (to be measured with the strain gauge installed on the input bar) reflected from the rear end of the input bar progresses to the front end thereof, reaches its front end at which the first reflected strain wave is reflected (second reflected strain wave). Thus, when the input bar is short, it is difficult to measure a correct strain amount of the reflected strain wave, because the second reflected strain wave is also measured with the strain gauge installed on the input bar, with the first and second reflected strain wave interfering with each other. Accordingly, it is necessary to space the strain gauge at an appropriate interval from the front end of the input bar to damp the second reflected strain wave. It is also necessary to space the strain gauge for measuring the incident strain wave and the strain gauge for measuring the first reflected strain wave at a required interval because near the rear end of the input bar, the incident strain wave and the first reflected strain wave interfere with each other. For this reason, the input bar is required to be long.

On the other hand, because the strain gauge installed on the output bar measures only the transmitted strain wave, it can be installed near the front end of the output bar. Even though the output bar is short, the strain gauge is distant from the rear end of the output bar. Thus, the reflected strain wave is not measured with the strain gauge nor interferes with the transmitted strain wave.

However, in the conventional viscoelastic characteristic value-measuring apparatus, the length of the output bar is set equal to that of the input bar. As the output bar becomes long, the output bar becomes increasingly flexible. Consequently, the transmitted strain wave having a small strain amount is measured under the influence of noise. Further, the long output bar causes the viscoelastic characteristic value-measuring apparatus to be large.

SUMMARY OF THE INVENTION

The present invention has been made in view of the above-described situation. Thus, it is an object of the present invention to provide a viscoelastic characteristic value-measuring apparatus capable of correctly measuring the viscoelastic characteristic value of a specimen even though the specimen is made of a comparatively soft material.

To achieve the object, there is provided a viscoelastic characteristic value-measuring apparatus having an input bar and an output bar arranged in a straight line to sandwich a specimen made of a viscoelastic material therebetween; first and second strain gauges installed on the input bar to measure an incident strain wave generate when a front end of the input bar is hit and a reflected strain wave; and third and fourth strain gauges installed on the output bar to measure a transmitted strain wave transmitted from the input bar to the output bar through the specimen.

The input bar and the output bar are made of a viscoelastic material; a length of the output bar is set to a range from 500 mm to 2500 mm both inclusive; and a length of the input bar is set to a range from 1500 mm to 2500 mm both inclusive.

The reason the length of the output bar is set to the range from 500 mm to 2500 mm both inclusive is as follows: The transmitted strain wave is reflected by the rear end of the output bar. Thus, there is a fear that if the length of the output bar is less than 500 mm, the reflected strain wave is measured by the fourth and third strain gauges before the strain wave is damped. If the length of the output bar is more than 2500 mm, manufacturing accuracy deteriorates and the output bar is liable to flex in a larger amount. The flexure causes a noise to be generated in the strain wave and makes it difficult to make the axis of the input bar and that of the output bar to be coincident with each other, thus deteriorating measurement accuracy. From this point of view, preferably, the length of the output bar is in the range from 800 mm to 2200 mm both inclusive.

It is preferable that the length of the input bar is set to the range from 1500 mm to 2500 mm both inclusive.

That is, it is necessary to measure the incident strain wave with the first and second strain gauges of the input bar and also measure the reflected strain wave reflected from the rear end of the input bar after the incident strain wave is damped. Therefore, it is necessary to space the first strain gauge at a long interval from the rear end of the input bar and the second strain gauge at a long interval from the rear end thereof. The reflected strain wave reflected from the rear end of the input bar reaches the front end of the input bar after it is measured with the second and first strain gauges. If the length of the input bar is less than 1500 mm, the reflected strain wave is reflected again by the front end thereof, and the re-reflected strain wave is measured with the first and second strain gauges. Similarly to the output bar, the reason the length of the input bar is set to less than 2500 mm is as follows: If the length of the input bar is more than 2500 mm, manufacturing accuracy deteriorates and the input bar is liable to flex in a larger amount. The flexure makes it difficult to make the axis of the input bar and that of the output bar to be coincident with each other, thus deteriorating measurement accuracy. From this point of view, preferably, the length of the input bar is in the range from 1800 mm to 2300 mm both inclusive.

As described above, according to the present invention, the length of the output bar is set shorter than that of the input bar to measure the incident strain wave and the reflected strain wave in the input bar and the transmitted strain wave in the output bar with high accuracy.

Needless to say, the input bar and the output bar may have the same length and consist of the same bar and the length thereof may be in the range from 1500 mm to 2500 mm both inclusive.

The viscoelastic characteristic value-measuring apparatus of the present invention is to measure the viscoelastic characteristic value of a specimen made of the viscoelastic material such as rubber or elastic resin. Thus, a polymer, preferably, the polymer consisting of the viscoelastic material is used as the material of the input bar and the output bar. The use of the viscoelastic material as the input bar and the output bar permits decrease in the difference between the characteristic impedance of the specimen and that of the input bar and the output bar.

Therefore, as the viscoelastic material of the input bar and the output bar, it is preferable to selectively use the one which reduces the difference between the viscoelastic characteristic value thereof and that of the specimen.

As the material of the input bar and the output bar, it is possible to use the following viscoelastic materials: acrylic resin, polyvinyl chloride resin, polyacetal resin, polycarbonate resin. Of the above materials, the acrylic resin is favorably used. Polymethyl methacrylate is particularly preferable. The use of the viscoelastic material as the stress bar consisting of the input bar and the output bar allows decrease in the difference between the impedance of the specimen made of a soft viscoelastic material such as synthetic resin, cross-linked rubber, and the like and that of the stress bar.

The first strain gauge is installed on the input bar at a front side thereof, and the second strain gauge is installed thereon at a rear side thereof, such that the first strain gauge is located between a position spaced at an interval of 10% of a whole length of the input bar from a rear end thereof and a position spaced at an interval of 70% of the whole length thereof from the rear end thereof and that the second strain gauge is located between a position spaced at an interval of 8% of the whole length of the input bar from the rear end thereof and a position spaced at an interval of 62% of the whole length thereof from the rear end thereof.

More specifically, the first strain gauge is located in the range spaced at the interval of 300 mm –1500 mm and preferably, 750 mm–1000 mm from the rear end of the input bar; and the second strain gauge is located in the range spaced at the interval of 100 mm –1300 mm and preferably, 400 mm–750 mm from the rear end thereof.

That is, it is necessary to space the first strain gauge at 10% and the second strain gauge at 8% from the rear end of the input bar connected with the specimen. This is because if the first strain gauge and the second strain gauge are too close to the specimen, the second strain gauge and the first strain gauge measure a strain wave reflected from the rear end of the input bar before an incident strain wave is not damped. That is, the incident strain wave is measured, with the incident strain wave and the reflected strain wave interfering with each other. Thus it is difficult to measure the incident strain wave correctly.

It is necessary to space the first strain gauge at 30% and the second strain gauge at 38% from the front end of the input bar. The first reflected strain wave reflected from the rear end of the input bar advances and is measured with the second and first strain gauges and reaches the front end of the input bar. Then, the first reflected strain wave is reflected from the front end of the input bar and progresses toward the rear end thereof as a second reflected strain wave. If the first and second strain gauges are too close to the front end of the input bar, the first and second strain gauges measure the second reflected strain wave before damp of the second reflected strain wave is not completed. Thus, it is difficult to measure the first reflected strain wave correctly, because the first and second reflected strain wave are interfering each other.

The interval between the first strain gauge and the second strain gauge is favorably in the range from 200 mm to 1200 mm both inclusive and more favorably about 600 mm. If the interval between the first strain gauge and the second strain gauge is less than 200 mm, i.e., if the interval is too short, the accuracy of the transmission function is low. Considering the entire length of the input bar and the installing position of the first strain gauge and the second strain gauge on the input bar, preferably, the interval between the first strain gauge and the second strain gauge is set to less than 1200 mm. By installing them in this range, the generation of noise can be reduced.

The third strain gauge is installed on the output bar at a front side thereof, and the fourth strain gauge is installed thereon at a rear side thereof, such that the third strain gauge is located between a position spaced at an interval of 4% of a whole length of the output bar from a front end thereof and a position spaced at an interval of 25% of the whole length thereof from the front end thereof and that the fourth strain gauge is located between a position spaced at an interval of 8% of the whole length of the output bar from the front end thereof and a position spaced at an interval of 50% of the whole length thereof from the front end thereof.

More specifically, it is preferable that the third strain gauge is located in the range spaced at the interval of 30 mm–400 mm from the front end of the output bar and that the fourth strain gauge is located in the range spaced at the interval of 60 mm–800 mm from the front end of the output bar.

That is, it is necessary to space the third strain gauge at the interval of 4% and the fourth strain gauge at the interval of 8% from the front end of the output bar connected with the specimen. This is because if the third strain gauge and the fourth strain gauge are too close to the specimen, the problem of noise occurs.

If the third strain gauge and the fourth strain gauge are spaced at the interval of 25% or more and 50% or more from the front end of the output bar, respectively, the strain wave reflected by the rear end of the output bar is measured with the fourth strain gauge and the third strain gauge before the damp of the transmitted strain wave does not terminate. That is, it is difficult to measure the transmitted strain wave correctly owing to the interference of the incident strain wave and the reflected strain wave.

The interval between the third strain gauge and the fourth strain gauge is set to the range from 30 mm to 400 mm both inclusive. Preferably, third strain gauge and the fourth strain gauge are installed on the output bar at an interval of about 100 mm.

The reason the between the third strain gauge and the fourth strain gauge is set to the range from 30 mm to 400 mm both inclusive is as follows: If the interval therebetween is less than 30 mm, i.e., if the third strain gauge and the fourth strain gauge are too close to each other, the accuracy of a transmission function becomes low. The minimum interval between the first strain gauge and the second strain gauge of the input bar is set to 200 mm, whereas the minimum interval between the third strain gauge and the fourth strain gauge of the output bar is set to 30 mm. This is because the strain gauge can be installed on the output bar at a position near the front end thereof.

Considering the entire length of the output bar and the installing position of the third strain gauge and the fourth strain gauge on the output bar, it is preferable to set the interval between the third strain gauge and the fourth strain gauge to not more than 400 mm. Thereby, the generation of noise can be reduced.

The input bar and the output bar are so arranged that they can hold the specimen having a length in the range from 1 mm to 15 mm both inclusive.

In other words, the specimen having a length in the range from 1 mm to 15 mm is used. This is because the specimen is made of a soft material and thus it is necessary to prevent the axis of the input bar and that of the output bar from shifting away from each other. If the length of the specimen is less than 1 mm, the following two forces become so large that they are not ignorable, which may cause increase of measurement error: A frictional force to be generated between the front end of the specimen and the rear end of the input bar and between the rear end of the specimen and the front end of the output bar; and a radial inertial force in the specimen. On the other hand, if the length of the specimen is more than 15 mm, the axis of the input bar and that of the output bar may shift away from each other, which may cause measurement to be inaccurate.

Preferably, the specimen is longitudinally uniform in its sectional configuration and circular. If the specimen is sectionally rectangular, noise increases.

Preferably, the input bar and the output bar are also circular and have the same diameter. The diameter thereof is set to the range from 10 mm to 30 mm both inclusive and preferably, 20 mm. The diameter thereof is determined in dependence on the diameter of the specimen. Preferably, the sectional area of the input bar and the output bar is larger than that of the specimen by not less than 1.0 time and not more than three times. This is for the following reason: If the sectional area of the input bar and the output bar is less than that of the specimen by one time, the specimen deforms nonuniformly, which may cause measurement to be inaccurate. On the other hand, if the sectional area of the input bar and the output bar is more than that of the specimen by three times, the first reflected strain wave in the input bar and the transmitted strain wave in the output bar may become nonuniform.

Adhesiveness of the connection surface of the specimen to that of the input bar and the output bar is an important requirement. Thus, the material of the connection surface is finished as a flat surface and processed with high machining tolerances to increase its adhesiveness. Preferably, its friction coefficient $\mu$ is set to $\mu<0.1$.

The first and second strain gauges to be installed on the input bar and the third and fourth strain gauges to be installed on the output bar are identical to each other. An unidirection plastic strain gauge is used most favorably, because of unidirectional matter. However, strain gauges of other types can be used.

Preferably, the impact bar is made of the same material, namely, a viscoelastic material as that of the input bar and the output bar. Preferably, the surface of the impact bar is spherical to prevent an inappropriate contact between the front end of the input bar and the surface of the impact bar. Both the solid impact bar and the hollow impact bar can be used. The collision speed of the impact bar is set appropriately according to the use of specimen. The front end of the input bar is hit with the impact bar favorably at 1 m/s–70 m/s, more favorably at 5 m/s–68 m/s, and most favorably at 10 m/s–60 m/s. The impact force is selected according to the length and sectional area of the input bar, the output bar, and the specimen and the kind of the specimen.

The input bar and/or the output bar are movably installed on a base, the interval between the input bar and the output bar is adjustable according to the length of the specimen, and the input bar and/or the output bar can be fixed to the base at a position where the rear end of the input bar is in contact with the front end surface of the specimen and the front end of the output bar is in contact with the rear end surface of the specimen.

The present invention provides a method of measuring a viscoelastic characteristic value by using the viscoelastic characteristic value-measuring apparatus. The method comprises the steps of hitting a front end of an input bar, with a specimen put between a rear end of the input bar and a front end of an output bar to generate a strain wave including an incident strain wave, a reflected strain wave, and a transmitted strain wave propagating in the input bar, the specimen, and the output bar; measuring the incident strain wave and the reflected strain wave with first and second strain gauges installed on the input bar, and measuring a transmitted strain wave with third and fourth strain gauges installed on the output bar; estimating a history of the incident strain wave at the rear end of the input bar, a history of the reflected strain wave at the rear end of the input bar, and a history of the transmitted strain wave at the front end of the output bar by using a history of the each strain wave; computing a strain speed history of a specimen, a strain history thereof, and a stress history thereof from the estimated history of the incident strain wave, the history of the reflected strain wave, and the history of the transmitted strain wave and determining a stress-strain curve of the specimen; and computing a viscoelastic characteristic value such as Young's modulus, a loss factor, and the like from the stress-strain curve.

In computing the strain speed history of the specimen, the strain history thereof, and the stress history thereof from the estimated history of the incident strain wave, the history of the reflected strain wave, and the history of the transmitted strain wave and determining a stress-strain curve of the specimen, it is preferable to use a viscoelastic constant of each of the input bar and the output bar.

The viscoelastic constant of each of the input bar and the output bar made of the same material as that of the input bar is a least squares of the error between a dynamic stress obtained by measuring a sample made of the same material as that of the input bar and the output bar with the viscoelastic characteristic value-measuring apparatus and a stress obtained by computation.

The stress obtained by computation means a stress obtained by performing computation by using a 3 factor's solid model, based on the dynamic stress obtained by measuring the sample.

In the measuring method of the present invention, a scattered wave which is generated by hitting the input bar with the impact bar is included as a component of the waveform to be measured by each gauge. The frequency of the strain wave is in the range of 2.5 kHz to 5.0 kHz, whereas the scattered wave is a high-frequency wave having a frequency of more than 10 kHz. The high-frequency wave is a noise. Thus, when a stress-strain curve is drawn by using the synthesized wave including a noise, the accuracy of the obtained viscoelastic characteristic value is low. Therefore, to improve the accuracy of the viscoelastic characteristic value, it is preferable to make a correction for the synthesized wave. As means for making the correction, a strain wave (synthesized wave) measured with the first, second, third, and fourth gauges is applied to a low-pass filter to remove a high-frequency wave whose frequency is more than 10 kHz.

A value measured with the strain gauge should be zero until the strain wave reach it. But actually, a slight amount of noise is inputted to the strain gauge. Thus, the value measured with the strain gauge deviates from zero. The deviation is slight. Because the history of strain is the integral of a strain speed, the deviation is added with the elapse of time and thus not ignorable. More specifically, it becomes difficult to specify the start point of the strain and the absolute value of the strain becomes inaccurate. Therefore, the accuracy of the obtained viscoelastic characteristic value is low. To improve the accuracy, a zero correction of making a base line value of a history of a strain wave zero is performed.

The stress history and the strain history form a smooth curve, respectively. According to the measuring method, the curve is smooth for a certain period of time after a time corresponding to a peak and becomes irregular. This is because the axis of the input bar and that of the output bar are not coincident with each other. It is difficult to make both axes coincident with each other. When the specimen is made of soft material, it is very difficult to make both axes coincident with each other. When computation is performed by using the curve having the irregular region, the accuracy of an obtained viscoelastic characteristic value is low. To improve measurement accuracy, it is preferable to perform a correction of making the irregular region smooth.

The strain history can be corrected as follows: A relaxation time $\lambda$ is derived by using a tangent at a predetermined point of an initial stage (namely, stage in which curve is smooth) of a computed strain history of a specimen after a peak. Then, a curve determined by using an equation (1) shown below is set as the curve after the predetermined point.

$$\epsilon(t)=\epsilon 0 \cdot t^{-t/\lambda} \tag{1}$$

where $\epsilon 0$ is a strain at the point of contact. The relaxation time $\lambda$ is determined from the intersection of the tangent and the time base.

The stress time history can be corrected as follows: A relaxation time $\lambda$ is derived by using a tangent at a predetermined point of an initial stage (namely, stage in which curve is smooth) of a computed stress history of the specimen after a peak. Then, a curve determined by using an equation (2) shown below is set as the curve after the predetermined point.

$$\sigma(t) = \sigma 0 \cdot e^{-t/\lambda} \quad (2)$$

where σ 0 is a stress at point of contact.

DETAILED DESCRIPTION OF THE PREFERRED EMBODIMENTS

The embodiment of the present invention will be described below with reference to the drawings.

Figure 1:
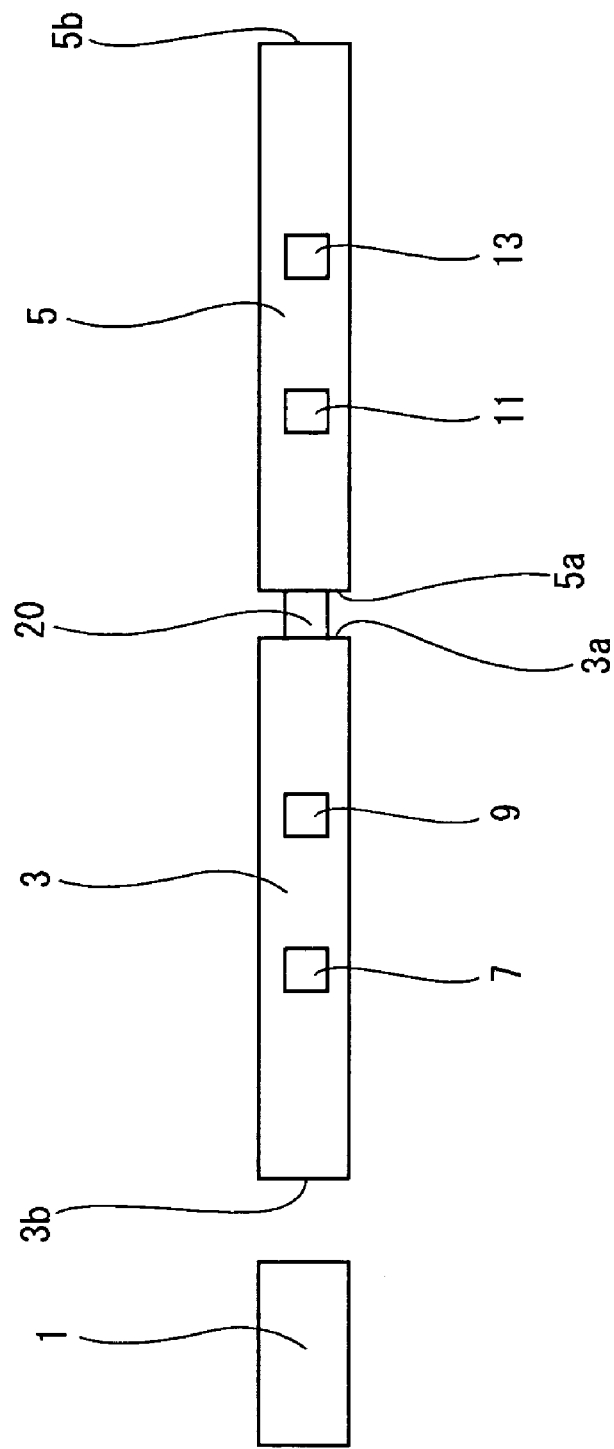
FIG. 1 is an illustrative front view showing a viscoelastic characteristic value-measuring apparatus according to an embodiment of the present invention.

FIG. 1 is an illustrative front view showing a viscoelastic characteristic value-measuring apparatus according to a first embodiment of the present invention. The viscoelastic characteristic value-measuring apparatus has an impact bar 1, an input bar 3, and an output bar 5. A first strain gauge 7 and a second strain gauge 9 are installed on the input bar 3. A third strain gauge 11 and a fourth strain gauge 13 are installed on the output bar 5. A cylindrical specimen 20 made of an viscoelastic material is put between a rear end 3a of the input bar 3 and a front end 5a of the output bar 5.

The impact bar 1, the input bar 3, and the output bar 5 are cylindrical and made of polymethyl methacrylate. The sectional diameter of each of the bars is 20 mm. The length of the impact bar 1, the input bar 3, and the output bar 5 are 100 mm, 1800 mm, 1000 mm, respectively.

The first strain gauge 7 is installed on the input bar 3 at a position spaced at 1200 mm from the rear end 3a thereof. The second strain gauge 9 is installed on the input bar 3 at a position spaced at 600 mm from the rear end 3a thereof. Thus, the first strain gauge 7 and the second strain gauge 9 are spaced at 600 mm. A third strain gauge 11 is installed on the output bar 5 at a position spaced at 100 mm from the front end 5a thereof. A fourth strain gauge 13 is installed on the output bar 5 at a position spaced at 200 mm from the front end 5a thereof. Thus, the third strain gauge 11 and the fourth strain gauge 13 are spaced at 100 mm.

As the first, second, third, and fourth strain gauges 7, 9, 11, and 13, a single axis plastic strain gauge is used. In the first embodiment, KFP-5-350-C1-65 manufactured by Kyowa Dengyo Ltd. is used as the single axis plastic strain gauge. The first, second, third, and fourth strain gauges 7, 9, 11, and 13 are bonded to the above-described positions of the input bar 3 and the output bar 5 such that first, second, third, and fourth strain gauges 7, 9, 11, and 13 are arranged in a straight line in the longitudinal direction of the viscoelastic characteristic value-measuring apparatus.

The length of the specimen 20, namely, the distance between the rear end 3a of the input bar 3 and the front end 5a of the output bar 5 is set to 4 mm. The sectional diameter of the specimen 20 is set to 18 mm. The specimen 20 used in the first embodiment has the length of 4 mm and is made of ionomer resin shaped cylindrically.

In measuring the viscoelastic characteristic value of the specimen made of the viscoelastic material with the viscoelastic characteristic value-measuring apparatus, initially, the specimen 20 is put between the input bar 3 and the output bar 5, with the front end surface of the specimen 20 in close contact with the rear end 3a of the input bar 3 and the rear end surface of the specimen 20 in close contact with the front end 5a of the output bar 5. In this state, the impact bar 1 is hit into the front end 3b of the input bar 3. Thereby, an incident strain wave is generated in the input bar 3. The incident strain wave advances to the rear end 3a of the input bar 3. A part of the incident strain wave is reflected by the rear end 3a of the input bar 3. The strain wave advances to the front end 3b of the input bar 3 as a reflected strain wave. A part of the incident strained passes through the specimen 20 from the rear end 3a of the input bar 3 and is propagated to the output bar 5. The strain wave advances to the rear end 5b of the output bar 5 as a transmitted strain wave.

The incident strain wave is measured with the first strain gauge 7 and the second strain gauge 9. A low-pass filter is used to remove a high-frequency wave having a frequency more than 10 KHz from the incident strain wave. Zero compensation of making the base line value of the history of the incident strain wave zero is performed. Fourier transformation is performed for an obtained time base strain at each the first strain gauge 7 and the second strain gauge 9 to determine a frequency axis strain. A transmission function is derived from the frequency axis strain at the first strain gauge 7 and the second strain gauge 9. In consideration of the ratio of the distance X1 between the first strain gauge 7 and the rear end 3a of the input bar 3 to the distance X2 between the second strain gauge 9 and the rear end 3a of the input bar 3, the frequency axis strain at the rear end 3a of the input bar 3 is estimated, based on the transmission function. Fourier inverse transformation is performed for the frequency axis strain to obtain the time base strain (history of strain) εi of the incident strain wave at the rear end 3a of the input bar 3.

Similarly, the reflected strain wave reflected from the rear end 3a of the input bar 3 and advancing to the front end 3b thereof is measured with the second strain gauge 9 and the first strain gauge 7. The time base strain (history of strain) εr of the reflected strain wave at the rear end 3a of the input bar 3 is obtained from the measured reflected strain wave.

The transmitted strain wave which is propagated to the output bar 5 through the specimen 20 is measured with the third strain gauge 11 and the fourth strain gauge 13 installed on the output bar 5. The time base strain (history of strain) εt of the transmitted strain wave at the front end 5a of the output bar 5 is obtained from the measured transmitted strain wave.

From the obtained εi, εr, and εt, the strain speed ε' of the specimen 20 is computed by using an equation (3) shown below.

$$\varepsilon' = (C0/L) \cdot (\varepsilon i - \varepsilon r - \varepsilon t) \quad (3)$$
$$= ((E/\rho)^{1/2}/L) \cdot (\varepsilon i - \varepsilon r - \varepsilon t)$$

where C0 indicates the propagation speed of the strain wave in the stress bar consisting of the input bar and the output bar; L indicates the length (m) of the specimen; E indicates the Young's modulus (N/m$^2$); and ρ indicates the density (kg/m$^3$) of the stress bar.

From the $\epsilon i$, $\epsilon r$, and $\epsilon t$, the strain $\epsilon$ of the specimen 20 is computed by using an equation (4) shown below.

$$\varepsilon = (C0/L) \cdot \int_0^t (\varepsilon i - \varepsilon r - \varepsilon t) dt \qquad (4)$$

$$= \left((E/\rho)^{\frac{1}{2}} / L\right) \cdot \int_0^t (\varepsilon i - \varepsilon r - \varepsilon t) dt$$

where C0 indicates the propagation speed (m/s) of a strain wave in the stress bar consisting of the input bar and the output bar; L indicates the length (m) of the specimen; E indicates the Young's modulus (N m$^2$); and $\rho$ indicates the density (kg/m$^3$) of the stress bar.

From the $\epsilon i$, $\epsilon r$, and $\epsilon t$, the stress $\sigma$ of the specimen 20 is computed by using an equation (5) shown below.

$$\sigma = = (E \cdot A / (2As)) \cdot (\varepsilon i + \varepsilon r + \varepsilon t) \qquad (5)$$

$$= (E \cdot D^2 / (2(Ds)^2)) \cdot (\varepsilon i + \varepsilon r + \varepsilon t)$$

where E indicates the Young's modulus (N/m$^2$) of the stress bar consisting of the input bar and the output bar; A indicates the sectional area (m$^2$) of the stress bar; As indicates the sectional area (M$^2$) of the specimen; D indicates the diameter of the stress bar; and Ds indicates the diameter of the specimen.

Figure 2:
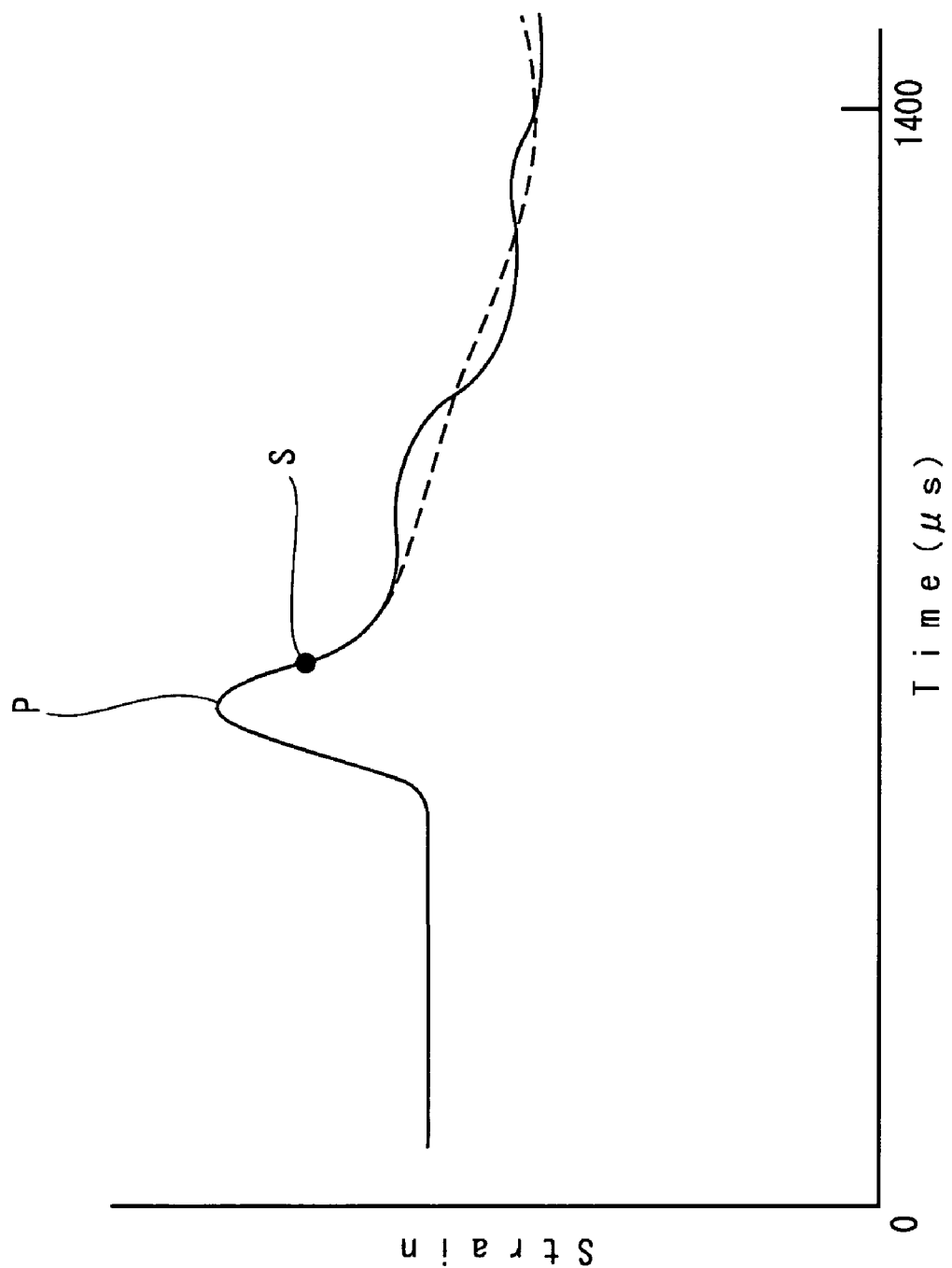
FIG. 2 is a graph showing a strain history of a specimen before compensation.

FIG. 2 shows the obtained strain history of the specimen 20. As shown in FIG. 2, the curve is smooth for a certain period of time after a time corresponding to a peak P. After a time corresponding to a given point of the graph FIG. 2, the curve becomes irregular. A point S is selected in the curve-smooth stage between the peak P and the given point. A tangent to the curve at the point S is drawn. A relaxation time $\lambda$ is derived from the intersection of the tangent and the time base. A curve found by using the equation (1) is determined as the curve after the point S of FIG. 2. In this manner, the entire strain history is corrected to a smooth curve (shown with a one-dot line). Thereby, it is possible to remove the influence of noise on an obtained viscoelastic characteristic value. Similarly, it is possible to make an entire stress history a smooth curve by using the equation (2). Thereby, it is possible to remove the influence of noise on an obtained viscoelastic characteristic value.

Figure 3:
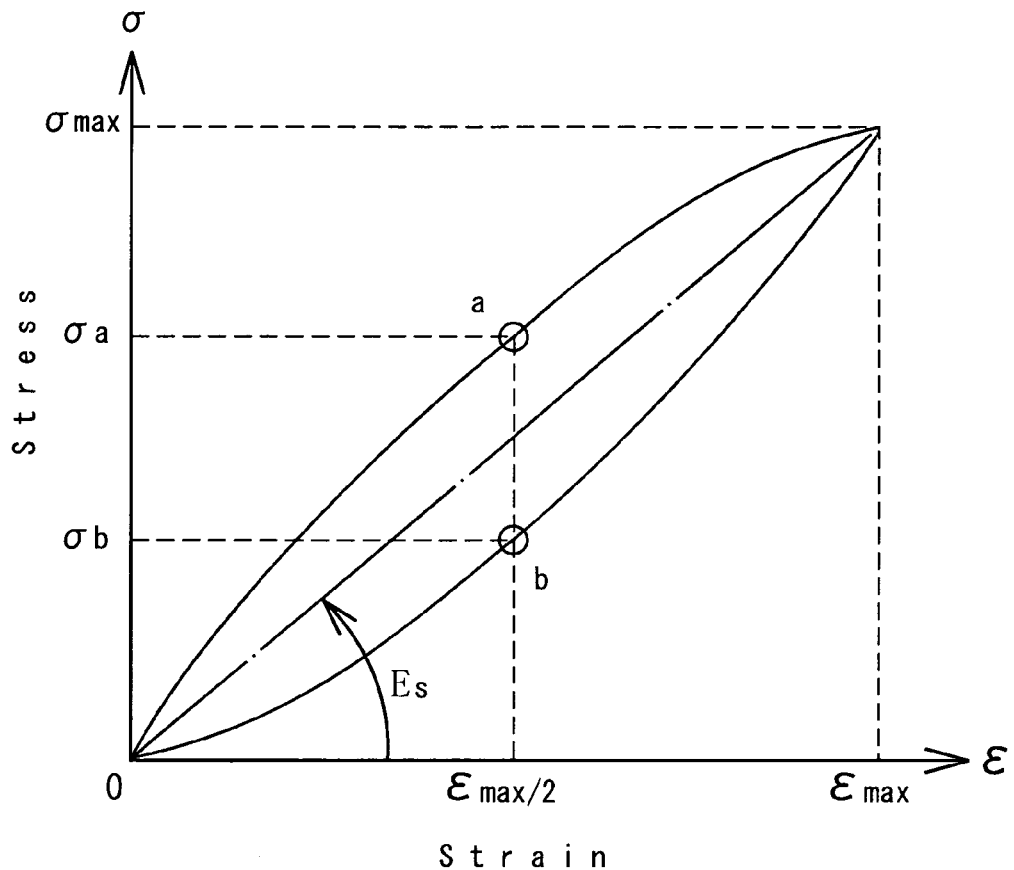
FIG. 3 is a graph showing a stress-strain curve.

A stress-strain curve is determined from the strain history and the stress history of the specimen 20 obtained by performing the above compensation. FIG. 3 is a graph showing a typical stress-strain curve. From the stress-strain curve, the Young's modulus Es of the specimen 20 is computed by using an equation (6) shown below.

$$Es = \sigma max / \epsilon max \qquad (6)$$

From the stress-strain curve of FIG. 3, a phase angle $\delta$ is computed by using an equation (7) shown below:

$$\delta = \sin^{-1}((\sigma a - \sigma b)/\sigma max) \qquad (7)$$

A loss factor (tan $\delta$) is computed from the phase angle $\delta$.

Measuring test of first—seventh examples and first—third comparison examples were conducted.

EXAMPLE I

Viscoelastic characteristic values of specimens were measured by using the viscoelastic characteristic value-measuring apparatus (length of input bar was 1800 mm and that of output bar was 1000 mm) of the first example shown in FIG. 1. The specimens were made of ionomer resin. The collision speed of the impact bar was 18.5 m/s. The room temperature was 23° C. The relative humidity was 50%.

The installing positions of the first and second strain gauges on the input bar and those of the third and fourth strain gauges on the output bar were as shown in table 1 shown below.

TABLE 1

| Length (mm) | First E | Second E | Third E | Fourth E | Fifth E | Sixth E | Seventh E | First CE | Second CE | Third CE |
|---|---|---|---|---|---|---|---|---|---|---|
| Length of input bar | 2000 | 1800 | 2500 | 1800 | 2000 | 1700 | 1500 | 1000 | 2800 | 1000 |
| Installing position of first strain gauge | 900 | 1200 | 600 | 400 | 1200 | 600 | 500 | 900 | 900 | 900 |
| Installing position of second strain gauge | 600 | 600 | 300 | 200 | 600 | 300 | 200 | 600 | 600 | 600 |
| Length of output bar | 2000 | 1000 | 1500 | 1800 | 1000 | 2500 | 1000 | 1000 | 2800 | 400 |
| Installing position of third strain gauge | 300 | 100 | 200 | 400 | 200 | 400 | 100 | 300 | 300 | 200 |
| Installing position of fourth strain gauge | 600 | 200 | 400 | 800 | 400 | 800 | 300 | 600 | 600 | 300 |
| Length of specimen | 4 | 12 | 8 | 6 | 5 | 10 | 7 | 4 | 18 | 4 |
| Overlapping of waves | ◎ | ◎ | ◎ | ○ | ◎ | ◎ | ○ | x | Impossible to measure | x |
| Noise | ◎ | ○ | ○ | ◎ | ◎ | ○ | ○ | ◎ | Impossible to measure | ◎ |

Where E denotes example, and CE denotes comparison example.

Installing position of first strain gauge: the interval from the rear end of the input bar (mm)
  Installing position of second strain gauge: the interval from the rear end of the input bar (mm)
  Installing position of third strain gauge: the interval from front end of the input bar (mm)
  Installing position of fourth strain gauge: the interval from the front end of the input bar (mm).

In the test of the second—seventh examples and the first—third comparison examples, the length of each of the input bar and the output bar shown in table 1, the installing positions of the first—fourth strain gauges, and the length of the specimen were differentiated, but other conditions (material of specimen and the like) were not differentiated.

Figure 4:
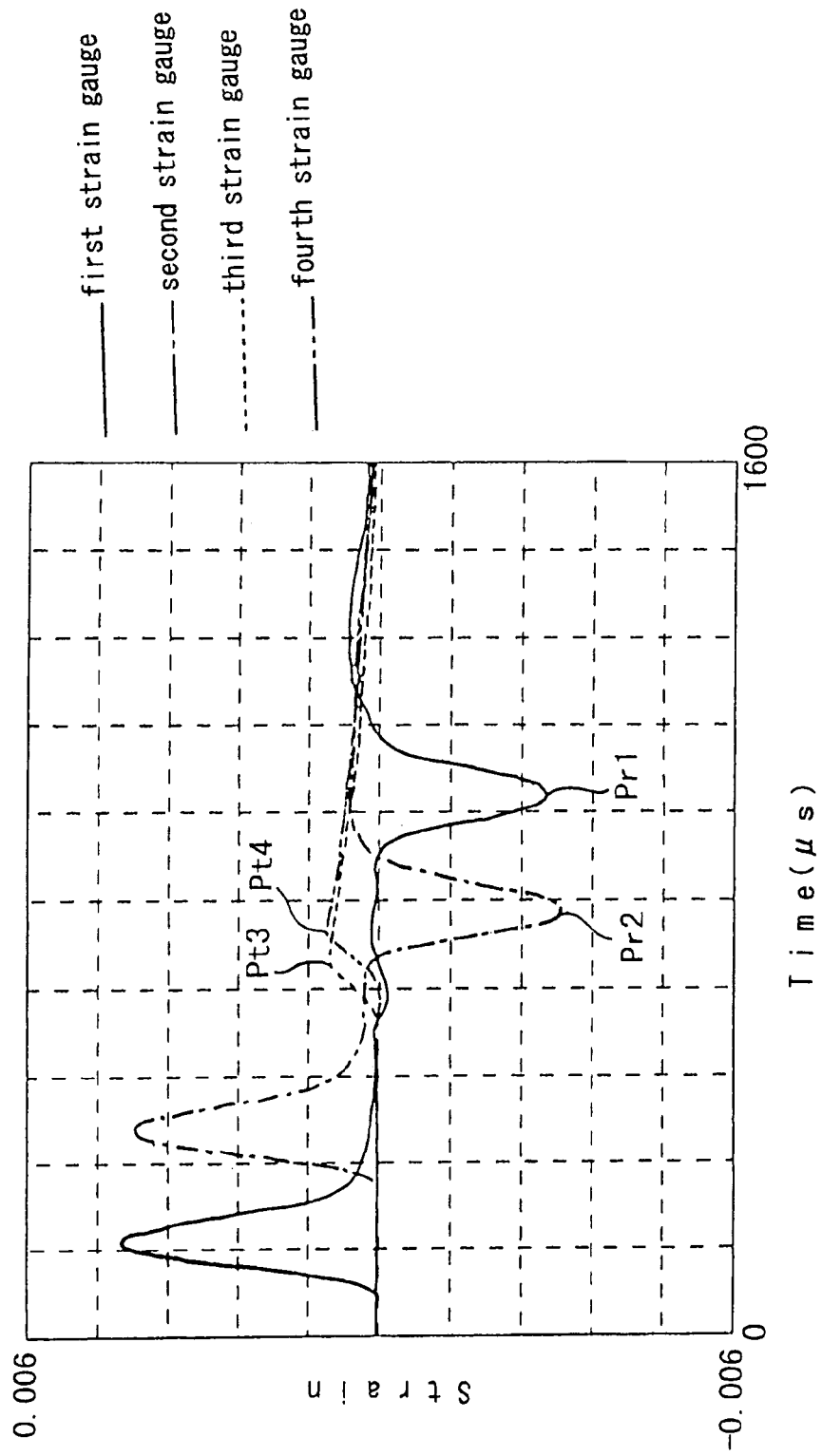
FIG. 4 is a graph showing a strain wave measured by a viscoelastic characteristic value-measuring apparatus of a first example of the present invention.

FIG. 4 shows the first example in which an incident strain wave and a reflected strain wave were measured with the first strain gauge and the second strain gauge of the first example, and a transmitted strain wave was measured with the third strain gauge and the fourth strain gauge.

As shown in FIG. 4, the result of the measurement of the first example was that peaks Pr1 and Pr2 of the reflected strain wave measured with the first and second strain gauges, respectively occurred once and overlapping of the waves did not occur, and that peaks Pt3 and Pt4 of the transmitted strain wave measured with the third and fourth strain gauges, respectively were present once and overlapping of the waves did not occur.

COMPARISON EXAMPLE

Figure 5:
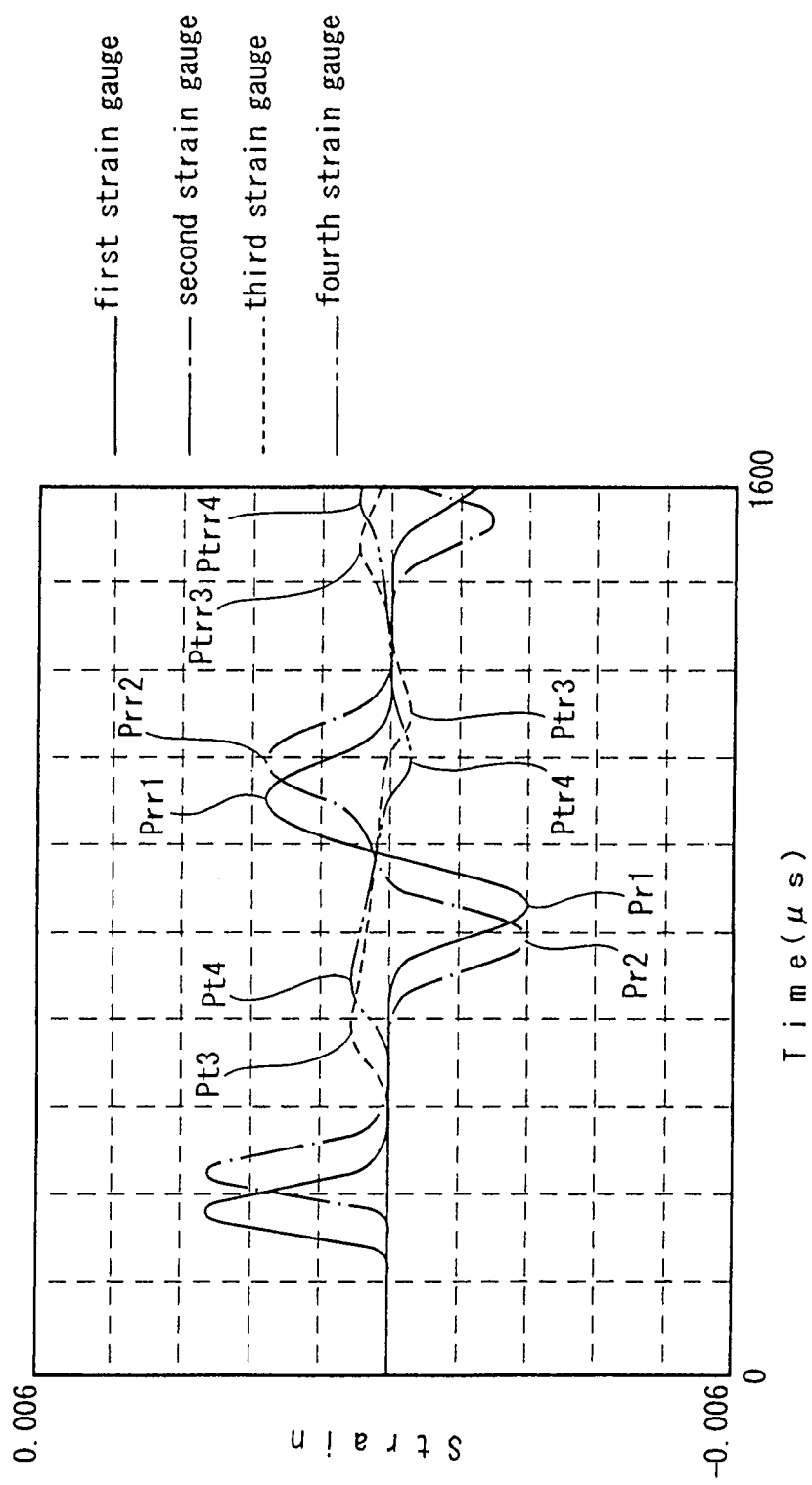
FIG. 5 is a graph showing a strain wave measured by a viscoelastic characteristic value-measuring apparatus of a first comparison example.

FIG. 5 shows the first comparison example in which the strain wave was measured with the first through fourth strain gauges.

In FIG. 5, Pr2 and Pr1 indicate peaks of a first reflected strain wave reflected from the rear end of the input bar.

Prr1 and Prr2 indicate peaks of a strain wave generated by the synthesis of a first reflected strain wave reflected from the rear end of the input bar when an incident strain wave was reflected thereat and a second reflected strain wave reflected from the front end of the input bar when the first reflected strain wave was reflected thereat again.

Pt3 and Pt4 indicate peaks of a transmitted strain wave measured at the output bar.

Ptr3 and Ptr4 indicate peaks of a strain wave generated by the synthesis of a strain wave reflected by the rear end of the output bar and the transmitted strain wave.

Ptrr3 and Ptrr4 indicate peaks of a strain wave generated by the synthesis of a first reflected strain wave reflected from the rear end of the output bar when an incident strain wave was reflected thereat and a second reflected strain wave reflected from the front end of the output bar when the first reflected strain wave was reflected thereat again.

As shown in FIG. 5, the first strain gauge measured the peak Pr1 of the first reflected strain wave reflected from the rear end of the input bar having the length of 1000 mm and the peak Prr1 of the second reflected strain wave reflected from the front end of the input bar when the first reflected strain wave was reflected thereat again. That is, before the damp of the second reflected strain wave does not terminate, the first reflected strain wave was measured, i.e., the first strain gauge measured the first and second reflected strain wave, which indicates that the first and second reflected strain wave interfered with each other.

Similarly, the second strain gauge measured the peak Pr2 of the first reflected strain wave reflected from the rear end of the input bar and the peak Prr2 of the second reflected strain wave reflected from the front end of the input bar when the first reflected strain wave was reflected thereat again.

In the first comparison example, the length of the output bar was 1001 mm. The third strain gauge was installed on the output bar at a position spaced at 300 mm from the front end of the output bar (700 mm from the rear end thereof). The fourth strain gauge was installed on the output bar at a position spaced at 600 mm from the front end of the output bar (400 mm from the rear end thereof). After the third and fourth strain gauges measured the peaks Pt3 and Pt4 of the transmitted strain wave, they measured the peaks Ptr3 and Ptr4 of the strain wave generated by the synthesis of the strain wave reflected from the rear end of the output bar and the transmitted strain wave and also the peaks Ptrr3 and Ptrr4 of the strain wave generated by the synthesis of the first reflected strain wave reflected from the rear end of the output bar and the second reflected strain wave reflected from the front end of the output bar.

On the other hand, in the second, fifth, and seventh examples in which the output bar having the same length of 1000 mm was used, the peak of the transmitted strain wave measured with the third and fourth strain gauges occurred once and no interference of waves was observed.

This is for the reason described below: In the second example, the third strain gauge was installed at the position of 100 mm from the front end of the output bar (900 mm from the rear end thereof) and the fourth strain gauge was installed at the position of 200 mm from the front end of the output bar (800 mm from the rear end thereof). Therefore, it is admitted that the reflected strain wave reflected from the rear end of the output bar was damped before it reached the third and fourth strain gauges. Similarly, in the fifth example, the third strain gauge was installed at the position of 200 mm from the front end of the output bar (800 mm from the rear end thereof) and the fourth strain gauge was installed at the position of 400 mm from the front end of the output bar (600 mm from the rear end thereof). In the seventh example, the third strain gauge was installed at the position of 100 mm from the front end of the output bar (900 mm from the rear end thereof) and the fourth strain gauge was installed at the position of 300 mm from the front end of the output bar (700 mm from the rear end thereof). Therefore, it is admitted that the reflected strain wave reflected from the rear end of the output bar was damped before it reached the third and fourth strain gauges.

The result indicates that when the third and fourth strain gauges were installed near the front end of the output bar, no overlapping of waves occurred even though the output bar was short.

In the second comparison example, the input bar and the output bar were as long as 2800 mm and the specimen was as long as 18 mm. Thus, much noise was generated and measurement could not be made.

In the third comparison example, the length of the output bar was set to 400 mm and the third strain gauge was installed at the position of 200 mm from the front end of the output bar (200 mm from the rear end thereof) and the fourth strain gauge was installed at the position of 300 mm from the front end of the output bar (100 mm from the rear end thereof). Thus, the strain wave reflected from the rear end of the output bar was measured with the fourth and third strain gauges.

In "overlapping of waves" of table 1, ⊚ indicates no overlapping of waves, ○ indicates that an assumed waveform was obtained although there was overlapping of waves, x indicates that because of overlapping of waves, a stress-strain curve was not obtained. In "noise", ⊚ indicates that no noise was generated, and ○ indicates that an assumed waveform was obtained although noise was generated.

The first through seventh examples had ⊚ or ○ and in the evaluation of "overlapping of waves" and had also ⊚ or ○ in the evaluation of noise.

In the first embodiment, the output bar was shorter than the input bar. But the length of the input bar may be equal to that of the output bar.

In the second embodiment, the input bar and the output bar had the same length of 2000 mm. The first strain gauge 7 was installed at the position of 900 mm from the rear end 3a of the input bar 3, and the second strain gauge 9 was installed at the position of 600 mm from the rear end 3a of the input bar 3. The third strain gauge 11 was installed at the position of 300 mm from the front end 5a of the output bar 5, and the fourth strain gauge 13 was installed at the position of 600 mm from the front end 5a of the output bar 5. The length of the specimen 20 was 4 mm, and the sectional diameter thereof was 18 mm.

EXAMPLE II

The viscoelastic characteristic value of the specimen was made of synthetic resin whose Shore hardness was 40 was measured. The impact speed of the impact bar was 14 m/s. Measurement was conducted at a room temperature of 23° C. and a relative humidity of 50%. A strain wave was measured with the first, second, third, and fourth strain gauges.

In the Example II, the measured strain wave was similar to that of the first example of Example I shown in FIG. 4. Reflected strain wave measured with the first and second gauges did not overlap with each other, and Transmitted strain wave measured with the third and fourth gauges did not overlap with each other.

As apparent from the foregoing description, in the viscoelastic characteristic value-measuring apparatus of the present invention using the split Hopkinson's bar, the length of the input bar and that of the output bar are set to an appropriate range. Further, the interval (namely, length of specimen) between the input bar and the output bar is set to an appropriate range. Furthermore, the input bar and the output bar are made of the viscoelastic material by which decrease is allowed in the difference between the characteristic impedance of the specimen made of the viscoelastic material and that of the input bar and the output bar. Therefore, the viscoelastic characteristic value-measuring apparatus can measure the viscoelastic characteristic value of the comparatively soft viscoelastic material such as resin and rubber with high accuracy.

The first and second strain gauges measuring the incident strain wave and the reflected strain wave are installed on the input bar at appropriate positions thereof, and the interval between them is appropriately set. Further, the third and fourth strain gauges measuring the transmitted strain wave are installed on the output bar at appropriate positions thereof, and the interval between them is appropriately set. Therefore, it is possible to detect the strain wave without interference. In this respect, the viscoelastic characteristic value-measuring apparatus has high measurement accuracy.

The conventional viscoelastic characteristic value-measuring apparatus using the split Hopkinson's bar is incapable of measuring the viscoelastic characteristic of a soft polymer consisting of rubber or resin when it deforms in a large amount (maximum deformation amount is in the range from 1% to 30%) and at a high speed (maximum strain speed: 500–8000 per second). This is because strain wave overlap each other. On the other hand, in the viscoelastic characteristic value-measuring apparatus using the split Hopkinson's bar, the length of the input bar and that of the output bar are specified to prevent overlap of strain wave which are detected with the strain gauges. Therefore, the viscoelastic characteristic value-measuring apparatus can measure the viscoelastic characteristic of the soft polymer accurately when it deforms in a large amount and at a high speed.

What is claimed is:

1. A viscoelastic characteristic value-measuring apparatus comprising:
    an input bar and an output bar arranged in a straight line to hold a specimen made of a viscoelastic material therebetween, wherein said length of said input bar is set to not less than 1500 mm and not more than 2500 mm, and said length of said output bar is set to not less than 500 mm and not more than 2500 mm;
    first and second strain gauges installed on said input bar to measure an incident strain wave generated when a front end of said input bar is hit and a reflected strain wave; and
    third and fourth strain gauges installed on said output bar to measure a transmitted strain wave transmitted from said input bar to said output bar through said specimen, wherein said input bar and said output bar are made of a viscoelastic material; and
    a length of said input bar is set so that the reflected strain wave is damped and a re-reflected strain wave is not generated.

2. The measuring apparatus according to claim 1, wherein the length of said output bar is relatively less than the length of said output bar.

3. The measuring apparatus according to claim 1, wherein said input bar and said output bar are made of a polymer.

4. The measuring apparatus according to claim 1, wherein said input bar and said output bar are made of a viscoelastic material whose viscoelastic characteristic value is different from that of the specimen in a small degree.

5. The measuring apparatus according to claim 1, wherein said first strain gauge is installed on said input bar at a front side thereof, and said second strain gauge is installed thereon at a rear side thereof, such that said first strain gauge is located between a position spaced at an interval of 10% of a whole length of said input bar from a rear end thereof and a position spaced at an interval of 70% of the whole length thereof from the rear end thereof and said second strain gauge is located between a position spaced at an interval of 8% of the whole length of said input bar from the rear end thereof and a position spaced at an interval of 62% of the whole length thereof from the rear end thereof.

6. The measuring apparatus according to claim 1, wherein said third strain gauge is installed on said output bar at a front side thereof, and said fourth strain gauge is installed thereon at a rear side thereof, such that said third strain gauge is located between a position spaced at an interval of 4% of the whole length of said output bar from a front end thereof and a position spaced at an interval of 25% of the whole length thereof from the front end thereof and said fourth strain gauge is located between a position spaced at an interval of 8% of the whole length of said output bar from the front end thereof and a position spaced at an interval of 50% of the whole length thereof from the front end thereof.

7. The measuring apparatus according to claim 1, wherein an interval between said first strain gauge and said second strain gauge is set to a range from 200 mm to 1200 mm both inclusive; and an interval between said third strain gauge and said fourth strain gauge is set to a range from 30 mm to 400 mm both inclusive.

8. The measuring apparatus according to claim 1, wherein said input bar and said output bar are circular and have the same sectional area; and a diameter thereof is set to a range from 10 mm to 30 mm both inclusive so that the sectional area thereof is larger than that of said specimen by not less than 1.0 time and not more than three times.

9. A method of measuring a viscoelastic characteristic value, comprising the steps of:
providing a measuring apparatus having an input bar and output bar;
setting a length of said input bar such that a reflected strain wave generated in the input bar when the input bar is hit is damped and a re-reflected strain wave is not generated, wherein said length of said input bar is set to not less than 1500 mm and not more than 2500 mm, and said length of said output bar is set to not less than 500 mm and not more than 2500 mm;
making a base line value of a history of a strain wave zero by performing a zero correction at the rear end of said input bar and at the front end of said output bar;
hitting a front end of said input bar, with a specimen held between a rear end of said input bar and a front end of an output bar to generate a strain wave including an incident strain wave, the reflected strain wave, and a transmitted strain wave propagating in said input bar, said specimen, and said output bar;
measuring said incident strain wave and said reflected strain wave with first and second strain gauges installed on said input bar, and measuring a transmitted strain wave with third and fourth strain gauges installed on said output bar;
computing a strain speed history of a specimen, a strain history thereof, and a stress history thereof from said estimated history of said incident strain wave, said history of said reflected strain wave, and said history of said transmitted strain wave and determining a stress-strain curve of said specimen; and
computing a viscoelastic characteristic value including Young's modulus or a loss factor, from said stress-strain curve.

10. The method according to claim 9, wherein the strain speed history of said specimen, the strain history thereof, and the stress history thereof are computed by using a viscoelastic constant of each of said input bar and said output bar to determine the stress-strain curve of said specimen.

11. The method according to claim 9, wherein a low-pass filter is used to perform a correction of removing a high-frequency wave having a frequency more than 10 kHz from a strain wave measured with said first, second, third, and fourth strain gauges.

12. The method according to claim 9, wherein a relaxation time $\lambda$ is derived by using a tangent at a predetermined point of an initial stage of a computed strain history of a specimen after a peak to correct said strain history after said predetermined point;

$$\epsilon(t)=\epsilon 0 \cdot e^{-t/\lambda} \quad (1) \text{ and}$$

where $\epsilon 0$ is a strain at the point of contact;
a relaxation time $\lambda$ is derived by using a tangent at a predetermined point of an initial stage of a computed stress history of said specimen after a peak to correct said stress history after said predetermined point;

$$\sigma(t)=\sigma 0 \cdot e^{-t/\lambda} \quad (2)$$

where $\sigma 0$ is a stress at the point of contact.

13. The method according to claim 9, wherein a length of a specimen is set to a range from 1 mm to 15 mm both inclusive.

14. The method according to claim 9, wherein a front end of said input bar is hit with an impact bar at an impact speed of 1 m/s –70 m/s.

15. The measuring apparatus according to claim 1, further comprising:
an impact bar for hitting the front end of the input bar.

16. The measuring apparatus according to claim 15, wherein the specimen includes a viscoelastic material having a viscoelastic characteristic that a maximum strain speed generated at the specimen is 500–8000 per second, when the front end of the input bar is hit with the impact bar at an impact speed of 1 m/s –70 m/s.

17. The measuring apparatus of claim 1, wherein the apparatus measures the strain generated at the specimen when it deforms in a relatively large amount and at a relatively high speed.

18. The method according to claim 9, wherein the maximum strain speed generated at the specimen is 500–8000 per second, when the front end of the input bar is hit with a impact bar.

19. The method of claim 9, wherein the viscoelastic characteristic value for the specimen is computed when the specimen deforms in a relatively large amount at a relative high speed.

20. The measuring apparatus according to claim 1, wherein the specimen has a characteristic maximum strain deformation amount in the range from 1% to 30%.

21. The method according to claim 9, wherein the specimen has a characteristic maximum strain deformation amount in the range from 1% to 30%.

22. The measuring apparatus according to claim 1, wherein said length of said output bar is set to not less than 500 mm nor more than 2500 mm, and said length of said input bar is set to not less than 1500 mm nor more than 2500 mm.

23. The method according to claim 9, wherein said length of said output bar is set to not less than 500 mm nor more than 2500 mm, and said length of said input bar is set to not less than 1500 mm nor more than 2500 mm.

* * * * *